United States Patent
Mausner

Patent Number: 5,922,331
Date of Patent: Jul. 13, 1999

[54] SKIN CREAM COMPOSITION

[75] Inventor: Jack Mausner, New York, N.Y.

[73] Assignee: Chanel, Inc., Piscataway, N.J.

[21] Appl. No.: 08/824,524

[22] Filed: Mar. 26, 1997

[51] Int. Cl.$^6$ .................................................... A61K 7/48

[52] U.S. Cl. ..................... 424/401; 424/195.1; 514/844; 514/846

[58] Field of Search .............................. 424/401, 195.1; 514/844, 846

[56] References Cited

U.S. PATENT DOCUMENTS

| | | | |
|---|---|---|---|
| 3,697,643 | 10/1972 | Shepherd et al. | 424/401 |
| 3,864,275 | 2/1975 | Kan et al. | 424/450 |
| 3,911,105 | 10/1975 | Papantoniou et al. | 424/401 |
| 3,966,398 | 6/1976 | Vanlerberghe et al. | 424/70.1 |
| 4,125,549 | 11/1978 | Coopersmith et al. | 424/401 |
| 4,247,411 | 1/1981 | Vanlerberghe et al. | 424/450 |
| 4,369,037 | 1/1983 | Matsunaga et al. | 424/70.1 |
| 4,400,295 | 8/1983 | Ootsu et al. | 424/401 |
| 4,423,031 | 12/1983 | Murui et al. | 424/63 |
| 4,460,371 | 7/1984 | Abber | 424/448 |
| 4,481,186 | 11/1984 | Deckner | 424/59 |
| 4,549,990 | 10/1985 | Seguin et al. | 552/545 |
| 4,574,082 | 3/1986 | Tietjen et al. | 424/63 |
| 4,752,496 | 6/1988 | Fellow et al. | 424/490 |
| 4,758,599 | 7/1988 | Minetti | 424/73 |
| 4,820,510 | 4/1989 | Arraudeau et al. | 424/63 |
| 4,883,659 | 11/1989 | Goodman et al. | 424/78.03 |
| 4,925,667 | 5/1990 | Fellows et al. | 424/401 |
| 4,927,952 | 5/1990 | Gueyne et al. | 556/419 |
| 4,952,560 | 8/1990 | Kigasawa et al. | 514/773 |
| 4,980,155 | 12/1990 | Shah et al. | 424/63 |
| 4,988,502 | 1/1991 | Qunanian et al. | 424/63 |
| 5,034,226 | 7/1991 | Beck | 424/195.1 |
| 5,037,803 | 8/1991 | Gueyne et al. | 424/59 |
| 5,053,220 | 10/1991 | Arraudeau et al. | 424/63 |
| 5,053,221 | 10/1991 | Robertson et al. | 424/63 |
| 5,061,481 | 10/1991 | Suzuki et al. | 424/63 |
| 5,093,109 | 3/1992 | Mausner | 424/63 |
| 5,116,607 | 5/1992 | Jones | 424/70.14 |
| 5,182,103 | 1/1993 | Nakane et al. | 424/78.03 |
| 5,204,105 | 4/1993 | Mausner | 424/401 |
| 5,215,759 | 6/1993 | Mausner | 424/489 |
| 5,254,331 | 10/1993 | Mausner | 424/59 |
| 5,352,441 | 10/1994 | Mausner | 424/64 |
| 5,391,373 | 2/1995 | Mausner | 424/401 |
| 5,571,503 | 11/1996 | Mausner | 424/59 |

*Primary Examiner*—Jyothsna Venkat
*Attorney, Agent, or Firm*—Merchant, Gould, Smith Edell, Welter & Schmidt

[57] ABSTRACT

An improved skin cream composition according to the present invention provides protection against lumpiness, edema, and other effects of liposuction and cosmetic surgery, as well as increasing the smoothness of the skin. In general, a skin cream composition according to the present invention comprises: water, and emulsified and dispersed in the water: (1) a long-chain fatty acid ester of ascorbic acid; (2) a short-chain carboxylic acid ester of tocopherol; (3) a glyceryl ester complex comprising at least one glyceryl ester selected from the group consisting of glyceryl linoleate, glyceryl linolenate, and glyceryl arachidonate; (4) a first complex consisting essentially of water, propylene glycol, lecithin, caffeine benzoate, and palmitoyl carnitine; (5) a second complex consisting essentially of water, caffeine, carnitine, and hydrolyzed glycosaminoglycans; (6) a third complex consisting essentially of glycerol, butcher broom extract, passion flower extract, glycogen, hydrolyzed collagen, and PEG 6-32; (7) calendula extract; (8) a water-glycol extract of chamomile; (9) hydrophilic microcapsules; (10) lipophilic microcapsules; and (11) microcapsules comprising methylsilanol elastinate. Other, optional cosmetic ingredients and ancillary ingredients can also be used.

44 Claims, No Drawings

SKIN CREAM COMPOSITION

BACKGROUND

This invention is directed to an improved skin cream composition.

Modern environmental conditions, such as heating and air conditioning, exposure to the sun, and environmental pollution, exert severe stress on the skin and accelerate the natural aging process, resulting in wrinkles, loss of firmness and elasticity, age spots, discoloration, dryness, and other cosmetically undesirable effects. In addition, cosmetic surgery such as liposuction can cause additional damage to skin, resulting in effects such as lumping and edema.

Although a number of cosmetic compositions for use on the skin already exist, there is a need for a simple-to-apply and effective all-in-one cosmetic treatment, such as a skin cream composition, that can promote significant retexturizing of the skin, increase its smoothness and firmness, while at the same time acting against skin damage resulting from cosmetic surgery such as liposuction.

SUMMARY

I have developed a skin cream composition incorporating a new combination of ingredients particularly designed to provide protection against skin damage occurring after liposuction, such as lumping and edema.

In general, such a skin cream composition comprises: water, and emulsified and dispersed in the water:

(1) a long-chain fatty acid ester of ascorbic acid;

(2) a short-chain carboxylic acid ester of tocopherol;

(3) a glyceryl ester complex comprising at least one glyceryl ester selected from the group consisting of glyceryl linoleate, glyceryl linolenate, and glyceryl arachidonate;

(4) a first complex consisting essentially of water, propylene glycol, lecithin, caffeine benzoate, and palmitoyl carnitine;

(5) a second complex consisting essentially of water, caffeine, carnitine, and hydrolyzed glycosaminoglycans;

(6) a third complex consisting essentially of glycerol, butcher broom extract, passion flower extract, glycogen, hydrolyzed collagen, and PEG 6-32;

(7) calendula extract;

(8) a water-glycol extract of chamomile;

(9) hydrophilic microcapsules;

(10) lipophilic microcapsules; and

(11) microcapsules comprising methylsilanol elastinate.

Each of the long-chain fatty acid ester of ascorbic acid, the short-chain carboxylic acid ester of tocopherol, the glyceryl ester complex, the first complex, the second complex, the third complex, the calendula extract, the water-glycol extract of chamomile, the hydrophilic microcapsules, the lipophilic microcapsules, and the microcapsules comprising methylsilanol elastinate are present in a quantity sufficient to increase the smoothness, decrease the lumpiness, or decrease the edema of skin to which the composition is applied.

The skin cream composition can comprise additional, optional cosmetic components: aloe vera gel, glycosaminoglycans, and nylon-12. Preferably, the skin cream composition comprises all of aloe vera gel, glycosaminoglycans, and nylon-12.

The long-chain fatty acid ester of ascorbic acid can be selected from the group consisting of ascorbyl palmitate, ascorbyl myristate, and ascorbyl stearate. Preferably, the long-chain fatty acid ester of ascorbic acid is ascorbyl palmitate.

The short-chain carboxylic acid ester of tocopherol can be selected from the group consisting of tocopheryl acetate, tocopheryl propionate, and tocopheryl butyrate. Preferably, the short-chain carboxylic acid ester of tocopherol is tocopheryl acetate.

Preferably, the glyceryl ester complex comprises glyceryl linoleate, glyceryl linolenate, and glyceryl arachidonate.

Preferably, the hydrophilic microcapsules comprise in water:

(1) glycerol;
(2) chitin;
(3) sodium lactate;
(4) sodium pyrrolidone carboxylate;
(5) glycogen;
(6) urea;
(7) propylene glycol;
(8) sodium chloride;
(9) at least one amino acid selected from the group consisting of glycine, arginine, lysine, histidine, and ornithine; and
(10) hydrolyzed collagen.

Most preferably, the hydrophilic microcapsules comprise glycine, arginine, lysine, histidine, and ornithine.

Preferably, the lipophilic microcapsules comprise:

(1) glycosphingolipids;
(2) phospholipids;
(3) cholesterol;
(4) at least one long-chain saturated fatty acid selected from the group consisting of myristic acid, palmitic acid, stearic acid, and arachidic acid;
(5) squalane;
(6) a $C_{10}$–$C_{30}$ carboxylic acid ester of a sterol selected from the group consisting of cholesterol, lanosterol, and mixtures thereof; and
(7) octyldodecanol.

More preferably, the lipophilic microcapsules comprise stearic acid and palmitic acid.

Optionally, but more preferably, the lipophilic microcapsules further comprise a diglyceryl succinate of a medium-chain carboxylic acid selected from the group consisting of caprylic acid, capric acid, and mixtures thereof.

Preferably, the ascorbyl palmitate comprises about 0.02% of the composition, the tocopheryl acetate comprises about 0.5% of the composition, the glyceryl ester complex comprises about 0.5% of the composition, the first complex comprises about 3.0% of the composition, the second complex comprises about 2.0% of the composition, the third complex comprises about 0.0011% of the composition, the calendula extract comprises about 0.2% of the composition, the aloe vera gel comprises about 0.2% of the composition, the water-glycol extract of chamomile comprises about 0.2% of the composition, the glycosaminoglycans comprise about 1.0% of the composition, the hydrophilic microcapsules comprise about 0.25% of the composition, the lipophilic microcapsules comprise about 0.25% of the composition, the microcapsules comprising methylsilanol elastinate comprise about 0.25% of the composition, and the nylon-12 comprises about 1.2% of the composition.

Preferably, the skin cream composition of the present invention further comprises a lipid-soluble component. The lipid-soluble component can comprise at least one of dimethicone, bisabolol, polyoxyethylene fatty acid esters, cetyl alcohol, a glyceryl triester of a medium-chain carboxylic acid selected from the group consisting of tricaproin, tricaprylin, and tricaprin, and mixtures thereof, white petrolatum, and mineral oil. Preferably, the lipid-soluble component comprises all of dimethicone, bisabolol, polyoxyethylene fatty acid esters, cetyl alcohol, a glyceryl triester of a medium-chain carboxylic acid selected from the group consisting of tricaproin, tricaprylin, and tricaprin, and mixtures thereof, white petrolatum, and mineral oil, and the dimethicone comprises about 0.75% of the composition, the bisabolol comprises about 0.10% of the composition, the polyoxyethylene fatty acid esters comprise about 2.5% of the composition, the cetyl alcohol comprises about 4% of the composition, the tricaprylin comprises about 7.5% of the composition, the white petrolatum comprises about 3% of the composition, and the mineral oil comprises about 6.0% of the composition.

Preferably, the skin cream composition of the present invention comprises an emulsifier component. The emulsifier component can comprise at least one of a mixture of mono- and distearate esters of polyoxyethylene and free polyethylene oxide, partial esters of lauric, palmitic, stearic, and oleic acids and hexitol anhydrides, and 120-mole ethoxylated jojoba oil. Preferably, the emulsifier component comprises all of a mixture of mono- and distearate esters of polyoxyethylene and free polyethylene oxide, partial esters of lauric, palmitic, stearic, and oleic acids and hexitol anhydrides, and 120-mole ethoxylated jojoba oil, and the mixture of mono- and distearate esters of polyoxyethylene and free polyethylene oxide comprises about 1.25% of the composition, the partial esters of lauric, palmitic, stearic, and oleic acids and hexitol anhydrides comprise about 0.13% of the composition, and the 120-mole ethoxylated jojoba oil comprises about 1.0% of the composition.

The skin cream composition of the present invention can further comprise an antioxidant component. Preferably, the antioxidant component comprises a mixture of about 70% propylene glycol, about 20% propyl gallate, and about 10% citric acid, and the antioxidant component comprises about 0.0011% of the composition.

The skin cream composition of the present invention can further comprise a preservative component. The preservative component can comprise at least one of imidazolyl urea and a complex of propylene glycol, phenoxyethanol, chlorphenesin, and methylparaben. Preferably, the preservative component comprises imidazolyl urea and a complex of propylene glycol, phenoxyethanol, chlorphenesin, and methylparaben, the imidazolyl urea comprises about 0.0011% of the composition, and the complex of propylene glycol, phenoxyethanol, chlorphenesin, and methylparaben comprises about 2.5% of the composition.

The skin cream composition of the present invention can further comprise a solvent component. The solvent component can comprise at least one ingredient selected from the group consisting of ethylene glycol, propylene glycol and 1,3-butylene glycol. Preferably, the solvent component is 1,3-butylene glycol, and the 1,3-butylene glycol comprises about 4.0% of the composition.

The skin cream composition of the present invention can further comprise a thickener component. The thickener component can comprise at least one ingredient selected from the group consisting of alginate derivatives and pre-neutralized carbomer 430. Preferably, the thickener component comprises alginate derivatives and preneutralized carbomer 430, the alginate derivatives comprise about 0.2% of the composition and the preneutralized carbomer 430 comprises about 0.5% of the composition.

The skin cream composition of the present invention can further comprise a hydrophilic component. The hydrophilic component preferably comprises a polar complex consisting essentially of mannitol, arginine, serine, pyrrolidone carboxylate, sucrose, citrulline, glycogen, histidine, alanine, threonine, glutamic acid, and lysine, wherein the mannitol, the arginine, the serine, the pyrrolidone carboxylate, the sucrose, the citrulline, the glycogen, the histidine, the alanine, and the threonine each comprise from about 2% to about 20% of the polar complex, and the glutamic acid and lysine each comprise from about 0.1% to about 2.0% of the polar complex, and the polar complex comprises about 1.0% of the composition.

The skin cream composition of the present invention can further comprise fragrance. The use of fragrance is well known in the cosmetic art. Typically, the fragrance comprises about 0.45% of the composition.

A preferred skin cream composition according to the present invention comprises: water, and emulsified and dispersed in the water:

(1) ascorbyl palmitate;
(2) tocopherol acetate;
(3) a glyceryl ester complex comprising glyceryl linoleate, glyceryl linolenate, and glyceryl arachidonate;
(4) a complex consisting essentially of water, propylene glycol, lecithin, caffeine benzoate, and palmitoyl carnitine;
(5) a complex consisting essentially of caffeine, carnitine, and hydrolyzed glycosaminoglycans;
(6) a complex consisting essentially of glycerol, butcher broom extract, passion flower extract, glycogen, hydrolyzed collagen, and PEG 6-32;
(7) calendula extract;
(8) a water-glycol extract of chamomile;
(9) hydrophilic microcapsules comprising in water:
  (a) glycerol;
  (b) chitin;
  (c) sodium lactate;
  (d) sodium pyrrolidone carboxylate;
  (e) glycogen;
  (f) urea;
  (g) propylene glycol;
  (h) sodium chloride;
  (i) glycine;
  (j) arginine;
  (k) lysine;
  (l) histidine;
  (m) ornithine; and
  (n) hydrolyzed collagen;
(10) lipophilic microcapsules comprising:
  (a) glycosphingolipids;
  (b) phospholipids;
  (c) cholesterol;
  (d) stearic acid;
  (e) palmitic acid;
  (f) squalane;
  (g) a $C_{10}$–$C_{30}$ carboxylic acid ester of a sterol selected from the group consisting of cholesterol, lanosterol, and mixtures thereof;
  (h) a diglyceryl succinate of a medium-chain carboxylic acid selected from the group consisting of caprylic acid, capric acid, and mixtures thereof; and
  (i) octyldodecanol;
(11) microcapsules comprising methylsilanol elastinate;
(12) glycosaminoglycans;
(13) aloe vera gel;
(14) nylon-12;
(15) a lipid-soluble component comprising:
  (a) dimethicone;

(b) bisabolol;
(c) polyoxyethylene fatty acid esters;
(d) cetyl alcohol;
(e) white petrolatum;
(f) tricaprylin; and
(g) mineral oil;
(16) an emulsifier component comprising:
  (a) a mixture of mono- and distearate esters of polyoxyethylene and free polyethylene oxide;
  (b) partial esters of lauric, palmitic, stearic, and oleic acids and hexitol anhydrides; and
  (c) 120-mole ethoxylated jojoba oil;
(17) an antioxidant component comprising a mixture of 70% propylene glycol, 20% propyl gallate, and 10% citric acid;
(18) a preservative component comprising:
  (a) imidazolyl urea; and
  (b) a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(19) a solvent component comprising 1,3-butylene glycol;
(20) a thickener component comprising:
  (a) alginate derivatives; and
  (b) preneutralized carbomer 430; and
(21) a hydrophilic component comprising a polar complex consisting essentially of mannitol, arginine, serine, pyrrolidone carboxylate, sucrose, citrulline, glycogen, histidine, alanine, threonine, glutamic acid, and lysine, wherein the mannitol, the arginine, the serine, the pyrrolidone carboxylate, the sucrose, the citrulline, the glycogen, the histidine, the alanine, and the threonine each comprise from about 2% to about 20% of the polar complex, and the glutamic acid and the lysine each comprises from about 0.1% to about 2% of the polar complex.

A particularly preferred skin cream composition of the present invention comprises: water, and emulsified and dispersed in the water:
(1) about 0.75% of dimethicone;
(2) about 0.1% of bisabolol;
(3) about 0.02% of ascorbyl palmitate;
(4) about 0.5 of tocopherol acetate;
(5) about 0.5% of a glyceryl ester complex comprising glyceryl linoleate, glyceryl linolenate, and glyceryl arachidonate, wherein the glyceryl linoleate comprises from about 65% to about 85% of the complex, the glyceryl linolenate comprises from about 5% to about 15% of the complex, and the glyceryl arachidonate comprises from about 1% to about 5% of the complex;
(6) about 1.25% of a mixture of mono- and distearate esters of polyoxyethylene and free polyethylene oxides;
(7) about 0.13% of partial esters of lauric, palmitic, stearic, and oleic acids and hexitol anhydrides;
(8) about 1.0% of 120-mole ethoxylated jojoba oil;
(9) about 2.5% of polyoxyethylene fatty acid esters;
(10) about 4.0% of cetyl alcohol;
(11) about 3.0% of white petrolatum;
(12) about 7.50% of tricaprylin;
(13) about 6.0% of mineral oil;
(14) about 0.0011% of a mixture of 70% propylene glycol, 20% propyl gallate, and 10% citric acid;
(15) about 0.0011% of imidazolyl urea;
(16) about 2.5% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(17) about 4.0% of 1,3-butylene glycol;
(18) about 0.2% of alginate derivatives;
(19) about 0.5% of preneutralized carbomer 430;
(20) about 3.0% of a first complex consisting essentially of water, propylene glycol, lecithin, caffeine benzoate and palmitoyl carnitine;
(21) about 2.0% of a second complex consisting essentially of water, caffeine, carnitine, and hydrolyzed glycosaminoglycans;
(22) about 0.0011% of a complex consisting essentially of glycerol, butcher broom extract, passion flower extract, glycogen, hydrolyzed collagen, and PEG 6-32;
(23) about 0.2% of calendula extract;
(24) about 0.2% of aloe vera gel;
(25) about 0.2% of a water-glycol extract of chamomile;
(26) about 1.0% of a polar complex consisting essentially of mannitol, arginine, serine, pyrrolidone carboxylate, sucrose, citrulline, glycogen, histidine, alanine, threonine, glutamic acid, and lysine wherein the mannitol, the arginine, the serine, the pyrrolidone carboxylate, the sucrose, the citrulline, the glycogen, the histidine, the alanine, and the threonine each comprise from about 2% to about 20% of the complex, and the glutamic acid and the lysine each comprise from about 0.1% to about 2% of the complex;
(27) about 1.0% of glycosaminoglycans;
(28) about 0.25% of hydrophilic microcapsules, the hydrophilic microcapsules comprising in water:
  (a) from about 20% to about 40% glycerol;
  (b) from about 10% to about 20% chitin;
  (c) from about 5% to about 15% each of sodium lactate and sodium pyrrolidone carboxylate;
  (d) from about 1% to about 5% each of glycogen, urea, propylene glycol, and sodium chloride;
  (e) up to about 1% each of glycine, arginine, lysine, histidine, and ornithine; and
  (f) up to about 1% of hydrolyzed collagen;
(29) about 0.25% of lipophilic microcapsules, the lipophilic microcapsules comprising:
  (a) from about 5% to about 15% each of glycosphingolipids, phospholipids, and cholesterol;
  (b) from about 1 to about 5% each of stearic acid, palmitic acid, squalane, and a $C_{10}$–$C_{30}$ carboxylic acid ester of a sterol selected from the group consisting of cholesterol, lanosterol, and mixtures thereof;
  (c) up to about 1% of a diglyceryl succinate of a medium-chain carboxylic acid selected from the group consisting of caprylic acid, capric acid, and mixtures thereof; and
  (d) from about 60% to about 80% of octyldodecanol;
(30) about 0.25% of microcapsules comprising methylsilanol elastinate;
(31) about 1.2% of nylon-12; and
(32) about 0.45% of fragrance.

These and other features, aspects, and advantages of the present invention will become better understood with reference to the following description, appended claims, and accompanying table where: table 5 shows the ingredients of a preferred embodiment of the present invention, their proportions, and the sequences of which they are a part for the purposes of mixing.

DESCRIPTION

A new combination of ingredients results in a skin cream composition that provides protection against many types of skin damage, particularly lumping and edema, as well as other types of skin damage that can occur after cosmetic surgery such as liposuction.

The skin cream composition of the present invention comprises an aqueous base in which cosmetic components are emulsified and dispersed. The cosmetic components include: (1) a long-chain fatty acid; (2) a short-chain carboxylic acid ester of tocopherol; (3) a glyceryl ester complex comprising at least one glyceryl ester selected from the group consisting of glyceryl linoleate, glyceryl linolenate, and glyceryl arachidonate; (4) a first complex consisting essentially of water, propylene glycol, lecithin, caffeine benzoate, and palmitoyl carnitine; (5) a second complex consisting essentially of water, caffeine, carnitine, and hydrolyzed glycosaminoglycans; (6) a third complex consisting essentially of glycerol, butcher broom extract, passion flower extract, glycogen, hydrolyzed collagen, and PEG 6-32; (7) calendula extract; (8) a water-glycol extract of chamomile; (9) hydrophilic microcapsules; (10) lipophilic microcapsules; (11) microcapsules comprising methylsilanol elastinate; (12) optionally, aloe vera gel; (13) optionally, glycosaminoglycans; and (14) optionally, nylon-12.

Typically, the skin cream composition of the present invention further comprises ancillary components such as: (1) a lipid-soluble component; (2) an emulsifier component; (3) an antioxidant component; (4) a preservative component; (5) a solvent component; (6) a thickener component; (7) a hydrophilic component; and (8) fragrance.

The ingredients included within these components are described in detail below.

The ingredients are dispersed in an emulsified composition by the method of preparation described below. "Dispersed" refers to any process by which the ingredients are uniformly distributed in the emulsified base, and includes dissolving, emulsifying, and forming a colloidal suspension.

I. NATURE AND PROPORTION OF INGREDIENTS OF THE SKIN CREAM COMPOSITION

A. The Cosmetic Components

Each of the cosmetic components disclosed above contributes to the improved properties of the cosmetic composition of the present invention and is present in a quantity sufficient to increase the smoothness, decrease the lumpiness, or decrease the edema of skin to which the composition is applied.

The optional cosmetic components provide additional beneficial effects.

Preferred compositions for these cosmetic components, including the optional cosmetic components, are now disclosed. However, other compositions containing the required ingredients set forth above are possible and are within the scope of the present invention.

1. The Long-Chain Fatty Acid Ester of Ascorbic Acid

The long-chain fatty acid ester of ascorbic acid can be selected from the group consisting of ascorbyl myristate, ascorbyl palmitate, ascorbyl stearate, and mixtures thereof. Preferably, the long-chain fatty acid ester of ascorbate is ascorbyl palmitate. Most preferably, the composition contains about 0.02% of ascorbyl palmitate.

2. The Short-Chain Carboxylic Acid Ester of Tocopherol

The short-chain carboxylic acid ester of tocopherol can be selected from the group consisting of tocopheryl acetate, tocopheryl propioniate, tocopheryl butyrate, and mixtures thereof. Preferably, the short-chain carboxylic acid ester is tocopheryl acetate. Preferably, the tocopheryl acetate comprises about 0.5% of the composition.

3. The Glyceryl Ester Complex

The glyceryl ester complex comprises at least one glyceryl ester selected from the group consisting of glyceryl linoleate, glyceryl linolenate, and glyceryl arachidonate. Preferably, the glyceryl ester complex comprises glyceryl linoleate, glyceryl linolenate, and glyceryl arachidonate. More preferably, the glyceryl ester complex comprises about 65% to about 85% glyceryl linoleate, about 5% to about 15% glyceryl linolenate, and about 1% to about 5% glyceryl arachidonate. Preferably, the glyceryl ester complex comprises about 0.5% of the composition.

4. The First Complex

The first complex consists essentially of water, propylene glycol, lecithin, caffeine benzoate, and palmitoyl carnitine. Preferably, the propylene glycol comprises about 20% to about 40% of the complex, the lecithin comprises about 1% to about 5% of the complex, the caffeine benzoate comprises about 1% to about 5% of the complex, and the palmitoyl carnitine comprises about 0.1% to about 2% of the complex. A suitable source of the first complex is marketed by Sederma under the name "Vexel". Preferably, the first complex comprises about 3% of the composition.

5. The Second Complex

The second complex consists essentially of water, caffeine, carnitine, and hydrolyzed glycosaminoglycans. Preferably, the complex comprises about 0.1% to about 2% caffeine, about 5% to about 20% carnitine, and about 0.1% to about 2.0% hydrolyzed glycosaminoglycans, with the remainder water. A suitable source of the second complex is marketed by Sederma under the name "Carnitiline". Preferably, the second complex comprises about 2.0% of the composition.

6. The Third Complex

The third complex consists essentially of glycerol, butcher broom extract, passion flower extract, glycogen, hydrolyzed collagen, and PEG 6-32. Preferably, the glycerol comprises about 40% to about 55% of the complex, the butcher broom extract comprises about 5% to about 20% of the complex, the passion flower extract comprises about 5% to about 20% of the complex, the glycogen comprises about 0.1% to about 2.0% of the complex, the hydrolyzed collagen comprises about 1% to about 5% of the complex, and the PEG 6-32 comprises about 5% to about 10% of the complex. A suitable source of the third complex is marketed by Lab Serobiologique of Somerville, N.J. under the name "Flavo Plasmine LS2704". Preferably, the third complex comprises about 0.011% of the composition.

7. Calendula Extract

The composition comprises calendula extract, a plant extract that provides firming and anti-edema properties. Preferably, calendula extract comprises about 0.2% of the composition.

8. Water-Glycol Extract of Chamomile

The composition further comprises a water-glycol extract of chamomile. This provides additional soothing properties. Preferably, chamomile extract comprises about 0.2% of the composition. A suitable source of a water-glycol extract of chamomile is Vegetol Hydroglycolique Chamomile MCF793, produced by Gattefosse Corporation.

9. Hydrophilic Microcapsules

The hydrophilic microcapsules used in skin cream compositions according to the present invention have a basic structure consisting of a microporous matrix of a polystyrene derived copolymer and enclosed water in which water-miscible compounds are dissolved and/or dispersed. The microcapsules are about 100 nm in diameter.

The hydrophobic microcapsules preferably comprise in water: (1) glycerol; (2) chitin; (3) sodium lactate; (4) sodium chloride; (5) sodium pyrrolidone carboxylate; (6) glycogen; (7) urea; (8) propylene glycol; (9) at least one amino acid selected from the group consisting of glycine, arginine, lysine, histidine, and ornithine; and (10) hydrolyzed collagen. Preferably, all of the amino acids glycine, arginine, lysine, histidine, and ornithine are present in the hydrophilic microcapsules.

A preferred range of composition for the hydrophobic microcapsules is as follows: glycerol, from about 20% to about 40%; chitin, from about 10% to about 20%; sodium lactate and sodium pyrrolidone carboxylate, from about 5% to about 15% each; glycogen, urea, propylene glycol, and sodium chloride, from about 1% to about 5% each; glycine, arginine, lysine, histidine, ornithine, and hydrolyzed collagen, up to about 1% each; and water, from about 15% to about 25%.

10. Lipophilic Microcapsules

The lipophilic microcapsules have a basic structure consisting of a coated core structure obtained by a controlled polymerization of polysiloxane, leading to a tridimensional lattice, coated by a polymeric shell. The lipophilic microcapsules are about 100 nm in diameter.

The lipophilic microcapsules preferably comprise: (1) octyldodecanol; (2) glycosphingolipids; (3) phospholipids; (4) cholesterol; (5) at least one long-chain saturated fatty acid selected from the group consisting of myristic acid, palmitic acid, stearic acid, and arachidic acid; (6) squalane; (7) a $C_{10}$–$C_{30}$ carboxylic acid ester of a sterol selected from the group consisting of cholesterol, lanosterol, and mixtures thereof; and, optionally, (8) a diglyceryl succinate of a medium-chain carboxylic acid selected from the group consisting of caprylic acid, capric acid, and mixtures thereof.

Glycosphingolipids comprise ceramide covalently bound to carbohydrate on the primary hydroxyl group of the ceramide. The carbohydrate is typically glucose, lactose, N-acetylglucosamine, N-acetylgalactosamine, or sialic acid.

The phospholipids can be phosphatidyl ethanolamine, phosphatidyl choline, phosphatidyl serine, phosphatidyl inositol, or diphosphatidyl glycerol.

Preferably, the long-chain fatty acids are palmitic acid and stearic acid.

A preferred range of compositions for the lipophilic microcapsules is: octyldodecanol from about 60% to about 80%; glycosphingolipids, phospholipids and cholesterol from about 5% to about 15% each; stearic acid, palmitic acid, squalane, $C_{10}$–$C_{30}$ the carboxylic acid ester of a sterol, from about 1% to about 5% each, and the diglyceryl succinate of a medium-chain carboxylic acid, up to about 1%.

Although Applicant does not intend to be bound by this theory, it is believed that the use of both hydrophilic and lipophilic microcapsules provide a moisturizing effect while at the same time preventing depletion of the essential oils of the skin. In addition, the encapsulation of the active ingredients provides slow release, and, therefore, contributes to long-lasting effects of the active ingredients.

11. The Methylsilanol Elastinate Microcapsules

The cosmetic composition according to the present invention further comprises microcapsules comprising an aqueous solution of methylsilanol elastinate. The microcapsules have a basic structure of a microporous matrix of a polystyrene derived copolymer. Methylsilanol elastinate is a derivative of the fibrous protein elastin. Although Applicant does not intend to be bound by this theory, it is believed that microcapsules containing methylsilanol elastinate exert a firming effect on the skin. The microcapsules comprising methylsilanol elastinate preferably comprise about 0.25% of the composition.

12. The Aloe Vera Gel

The use of the aloe vera gel is optional. If present, it preferably comprises about 0.2% of the composition. The aloe vera gel provides a soothing and calming effect on the skin.

13. Glycosaminoglycans

Optionally, but preferably, the cosmetic composition of the present invention can further comprise glycosaminoglycans. These glycolipid derivatives contribute to the restoration of the ground substance of the skin. Preferably, the glycosaminoglycans are obtained from snail mucus. A suitable complex is marketed by Sederma, Inc. of Brooklyn, N.Y., under the name "Hydraprotectol." Preferably, the glycosaminoglycans comprise about 1.0% of the composition.

14. Nylon-12

The cosmetic composition can further comprise, optionally, but preferably, nylon-12. A suitable preparation of nylon-12 is marketed by Lipo Chemical under the name "Orgasol 2002D." Preferably, the nylon-12 comprises about 1.2% of the composition.

B. The Ancillary Components

The ancillary components, whose use is optional but preferable, impart additional desirable properties to the skin cream composition of the present invention. These components can include: (1) a lipid-soluble component; (2) an emulsifier component; (3) an antioxidant component; (4) a preservative component; (5) a solvent component; (6) a thickener component; (7) a hydrophilic component; and (8) fragrance. Preferably, the composition of the present invention comprises all the ancillary components as indicated below:

1. The Lipid-Soluble Component

The skin cream composition of the present invention can further comprise a lipid-soluble component to provide added smoothness. The lipid-soluble component can comprise at least one ingredient selected from the group consisting of: (1) dimethicone; (2) bisabolol; (3) polyoxyethylene fatty acid esters; (4) cetyl alcohol; (5) a glyceryl triester of a medium-chain carboxylic acid selected from the group consisting of tricaproin, tricaprylin, tricaprin, and mixtures thereof; (6) white petrolatum; and (7) mineral oil.

Preferably, the glyceryl triester of the medium-chain carboxylic acid is tricaprylin.

Preferably, the lipid-soluble component comprises dimethicone, bisabolol, polyoxyethylene fatty acid esters, cetyl alcohol, tricaprylin, white petrolatum, and mineral oil.

Preferably, the dimethicone comprises about 0.75% of the composition, the bisabolol comprises about 0.1% of the composition, the polyoxyethylene fatty acid esters comprise about 2.5% of the composition, the cetyl alcohol comprises about 4% of the composition, the tricaprylin comprises about 7.5% of the composition, the white petrolatum comprises about 3% of the composition, and the mineral oil comprises about 6.0% of the composition.

A suitable preparation of polyoxyethylene fatty acid esters is Cerasynt SD, manufactured by Van Dyk & Co., Belleville, N.J. A suitable preparation of tricaprylin is Trivent OCG, manufactured by Trivent Chemical.

2. The Emulsifier Component

The skin cream composition of the present invention can further comprise an emulsifier component. Emulsifiers serve two functions. They act like a solubilizing agent to combine the water-soluble and non-water-soluble phases together; that is, to form a stable bridge between the waters and the oils of the ingredients. The emulsifiers also serve as emollients, providing a pleasant, esthetically appropriate tactile feeling when the emulsified composition is applied to the skin. The emulsifier component is present in a quantity sufficient to combine water-soluble and non-water-soluble phases of the composition.

The emulsifier component can comprise at least one of a mixture of mono- and distearate esters of polyoxyethylene and free polyethylene oxide, partial esters of lauric, palmitic, stearic, and oleic acids and hexitol anhydrides, and 120-mole ethoxylated jojoba oil. Preferably, the emulsifier component comprises a mixture of mono- and distearate esters of polyoxyethylene and free polyethylene oxide, partial esters of lauric, palmitic, stearic, and oleic acids and hexitol anhydrides and 120-mole ethoxylated jojoba oil. Preferably, the mixture of mono- and distearate esters of polyoxyethylene and free polyethylene oxide comprises about 1.25% of the composition, the partial esters of lauric, palmitic, stearic, and oleic acids and hexitol anhydrides comprise about 0.13% of the composition, and the 120-mole ethoxylated jojoba oil comprises about 1.0% of the composition.

A suitable preparation of mono- and distearate esters of polyoxyethylene and free polyethylene oxide is MYRJ 52, produced by Imperial Chemical Industries, Ltd., Macclesfield, Cheshire, England. A suitable preparation of partial esters of lauric, palmitic, stearic, and oleic acids and hexitol anhydrides is SPAN 65, produced by ICI. A suitable preparation of 120-mole ethoxylated jojoba oil is Solujoba E120, produced by Jojoba Growers and Process.

3. The Antioxidant Component

The skin cream composition according to the present invention can further comprise an antioxidant component. The antioxidant component prevents oxidation of the ingredients of the composition.

The antioxidant component can be a mixture of 70% propylene glycol, 20% propyl gallate, and 10% citric acid. Preferably, the antioxidant component comprises about 0.0011% of the composition.

A suitable mixture of propylene glycol, propyl gallate and citric acid in these proportions is available as Tenox S-1, manufactured by Eastman Kodak of Rochester, N.Y.

4. The Preservative Component

The skin cream composition according to the present invention preferably further comprises a preservative component. The preservative component is used to prevent the growth of microbes in the emulsified skin cream composition, which is typically manufactured under clean, but non-sterile conditions. The preservative component can comprise at least one of imidazolyl urea and a complex of propylene glycol, phenoxyethanol, chlorphenesin and methylparaben.

Preferably, the preservative component comprises both imidazolyl urea and a complex of propylene glycol, phenoxyethanol, chlorphenesin and methylparaben, the imidazolyl urea comprises about 0.0011% of the composition, and the complex of propylene glycol, phenoxyethanol, chlorphenesin and methylparaben comprises about 2.5% of the composition.

In the complex of propylene glycol, phenoxyethanol, chlorphenesin and methylparaben, the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex. A suitable complex of propylene glycol, phenoxyethanol, chlorphenesin and methylparaben is available as Elestab 388 from Lab Serobiologique of Somerville, N.J.

A suitable preparation of imidazolyl urea is available as Germall 115 from Sutton Labs.

5. The Solvent Component

Preferably, the skin cream composition according to the present invention preferably further comprises a solvent component. The use of a solvent component allows greater uniformity and ease of preparation. The solvent component can include at least one ingredient selected from the group consisting of ethylene glycol, propylene glycol, and 1,3-butylene glycol. Preferably, the solvent component comprises 1,3-butylene glycol and the solvent component comprises about 4.0% of the composition.

6. The Thickener Component

Preferably, skin cream compositions according to the present invention comprise a thickener component in a quantity sufficient to retain the composition when it is applied to the skin of a wearer. The thickener component comprise at least one ingredient selected from the group consisting of alginate derivatives and preneutralized carbomer 430. Preferably, the skin cream composition comprises both alginate derivatives and preneutralized carbomer 430. The alginate derivative preferably comprises about 0.2% of the composition, and the preneutralized carbomer 430 preferably comprises about 0.5% of the composition.

A suitable preparation of alginate derivatives is Keltrol CG, produced by Nutrasweet Kelco. A suitable preparation of preneutralized carbomer 430 is PNC-430, produced by Goodrich.

7. The Hydrophilic Component

A skin cream composition according to the present invention can further comprise a hydrophilic component. Preferably, the hydrophilic component comprises a polar complex consisting essentially of mannitol, arginine, serine, pyrrolidone carboxylate, sucrose, citrulline, glycogen, histidine, alanine, threonine, glutamic acid, and lysine. Preferably the polar complex comprises about 1.0% of the composition.

A suitable polar complex is Hydratyl 8453, from Lab Serobiologique, Inc., which comprises from about 2% to about 20% each of mannitol, arginine, serine, pyrrolidone carboxylate, sucrose, citrulline, glycogen, histidine, alanine, and threonine, and from about 0.1% to about 2% each of glutamic acid and lysine.

8. Fragrance

Preferably, the skin cream composition according to the present invention further comprises fragrance. The use of fragrance is well known in the cosmetic art, and need not be described further. Preferably, the fragrance comprises about 0.45% of the composition, although this can vary depending upon the fragrance used. A particularly preferred fragrance for use in cosmetic compositions according to the present invention is Cosmetic Concentrate RL224, produced by Chanel, Inc.

Cosmetic compositions according to the present invention can further comprise other components used in the cosmetic art, such as pigments and other conventional excipients. The use of such ingredients is well known in the cosmetic art and need not be described further here.

The preferred concentrations of both the cosmetic components, including the cosmetic components whose use is optional but preferred, and the ancillary components, are listed in FIG. 1 (Table I). Also shown in Table I are the sequences of which each component is a part for the preparation of the composition as disclosed below.

II. PREPARATION OF THE SKIN CREAM COMPOSITION

The various sequences and the orders in which they are prepared and combined for the preparation of the skin cream composition of the present invention are now described in detail. The sequences can be combined in a number of orders, of which the following disclosed below is representative but not exclusive. The object of the mixing sequence is to prepare a smooth and homogenous composition as an emulsion.

Sequence I (dimethicone, bisabolol, ascorbyl palmitate, tocopheryl acetate, diglyceryl ester complex, the mixture of mono- and distearate esters of polyoxyethylene and free polyethylene oxide, partial esters of lauric, palmitic, stearic, and oleic acids and hexitol anhydrides, 120-mole ethoxylated jojoba oil, polyoxyethylene fatty acid esters, cetyl alcohol, white petrolatum, tricaprylin, mineral oil, and the mixture of propylene glycol, propyl gallate, and citric acid) is loaded into a steam-lined kettle equipped with a high-speed mixture such as a Lightnin'™ mixer and heating is begun. Impeller mixing is begun when Mixture I becomes liquefied enough to start unhindered mixing of the impeller. The impeller speed is set at a rate fast enough not to create air. The target temperature for the oil phase is between 75–80° C. The ingredients are impeller mixed for 20 minutes within the 60–65° C. range. The oil phase is checked visually as it is mixing for unmelted wax particles and checked by stirring the bottom of the kettle with a paddle to lift any unmelted particles. If unmelted wax particles are present, additional impeller mixing time of 20 minutes is used. The mixing and temperature range of the oil phase (Sequence I) is maintained until its use later in the procedure.

Part of Sequence II (demineralized water) is metered into the proper size AGI kettle as required for the batch size. The sweep mixing speed is set to the 4–5 setting and the rest of Sequence II (imidazolyl urea and the complex of propylene glycol, phenoxyethanol, chlorphenesin, and methylparaben) is added. The temperature is maintained between 60–65° C. and the ingredients are mixed 20–25 minutes.

The ingredients of Sequence III (1,3-butylene glycol and alginate derivatives) are premixed with a stainless steel paddle to form a slurry. The resulting mixture should look like finely wetted sand. Mixing is continued until this appearance is obtained and there are no powder lumps present. Then slow homogenization mixing on the AGI kettle is started and the premixed slurry is then added to it. Mixing is continued with sweep mixing and slow homogenization mixing for 5 to 7 minutes. The temperature range is maintained between 60–65° and sweep mixing and slow homogenization mixing are maintained. Then the sweep mixing speed of the AGI kettle is slowed and the oil phase of Sequence I is transferred to the AGI kettle. The slow homogenization mixing should continue during transfer. After complete transfer of the oil phase of Sequence I, mixing action is maintained for 5–7 minutes before the remainder of the procedure is continued.

The ingredients of Sequence IV (tricaprylin and preneutralized carbomer 430) are premixed together in a clean, dry plastic drum or stainless steel container that is large enough to hold them using a stainless steel paddle. The powder is mixed into the liquid and the ingredients are mixed until the powder is dispersed and no lumps of powder are present.

The premixed Sequence IV is then added to the AGI kettle. After addition of the premixed Sequence IV, fast homogenization mixing is performed for 2–3 minutes and then slow homogenization mixing is continued. Slow homogenization mixing is continued for the remainder of the manufacturing process.

The mixed ingredients are then cooled slowly to 35–40° C. The cooling process should take 1.5 hours. The time length of cooling is essential in producing a smooth, emulsified product. When the temperature has reached the 35–40° C. range, Sequence V (the first complex consisting essentially of water, propylene glycol, lecithin, caffeine benzoate, and palmitoyl carnitine and the second complex consisting essentially of water, caffeine, carnitine, and hydrolyzed glycosaminoglycans) is added to the AGI kettle and mixed until homogenous.

Next, one gallon of water is metered into a container large enough to hold Sequence VI (the third complex consisting essentially of glycerol, butcher broom extract, passion flower extract, glycogen, hydrolyzed collagen, and PEG 6-32, calendula extract, the water-glycol extract of chamomile, the polar complex consisting essentially of mannitol, arginine, serine, pyrrolidone carboxylate, sucrose, citrulline, glycogen, histidine, alanine, threonine, glutamic acid, lysine, and glycosaminoglycans). A LAB impeller mixer is set up in the container of water. The impeller mixer is turned on and then the liquids in Sequence VI are added. The powder in Sequence VI is then added to the container. Impeller mixing is performed rapidly enough not to create air or foam. The ingredients are mixed until solubilized and no powder lumps are present. The mixed ingredients are then added to the AGI kettle and mixed until dispersed into the batch before the procedure is continued.

The ingredients of Sequence VII (hydrophilic microcapsules, lipophilic microcapsules, and microcapsules comprising methylsilanol elastinate) are added to the AGI kettle between 35–40° C. and mixed until the additions are dispersed.

Approximately 150–200 kg of bulk are then transferred from the AGI kettle to the C-9 kettle. The C-9 kettle should be a little over one-half filled. The impeller mixer is started and the powder of Sequence VIII (nylon-12) is added. Mixing speed is increased during addition being careful not to incorporate air into the mixture. The ingredients are mixed until the powder is dispersed.

Once the powder is dispersed, the mixture is transferred back to the AGI kettle. Sequence IX (fragrance) is added after the mixture has been transferred back to the AGI kettle. The ingredients are mixed for 5–7 minutes. After mixing in Sequence IX for 5–7 minutes, fast homogenization mixing is continued for 5–10 minutes to disperse all of the lumps from the mixture from the step of addition of Sequence VIII that was added to the AGI kettle. Fast homogenization mixing is continued until the lumps are gone and a smooth cream results.

With the batch between 35–40° C., deaeration is begun with vacuum for 45–60 minutes with sweep mixing set between 5–6. Top and bottom samples are taken for evaluation of the air present in the mixture versus a standard. If the batch does not match the standard, deaeration is continued in 30 minute increments until the batch meets the standard for air content. After deaeration, pressure is relieved and the batch is cooled to 20–25° C. When the temperature has reached 20–25° C., mixing is continued for one-half hour more. Top and bottom samples are checked for uniformity. When a sufficient degree of uniformity is present, the entire batch is run through the colloid mill at number 80 setting without circulation into stainless steel drums.

ADVANTAGES OF THE INVENTION

The skin cream composition of the present invention provides significantly improved retexturization of the skin, giving significantly improved smoothness. In particular, the cream is highly effective against lumping, edema, and other skin damage, particularly after liposuction or other cosmetic surgery that can cause damage to the skin. The composition is suitable for prolonged and repeated use.

Although the present invention has been described in considerable detail with regard to certain preferred versions thereof, other versions are possible. Therefore, the spirit and scope of the appended claims should not be limited to the descriptions of the preferred versions contained herein.

TABLE

| SEQUENCE | INGREDIENT | AMOUNT |
|---|---|---|
| I | Dimethicone | 0.75% |
| I | Bisabolol | 0.10% |
| I | Ascorbyl Palmitate | 0.02% |
| I | Tocopheryl Acetate | 0.50% |
| I | Glyceryl Ester Complex (Glyceryl Linoleate, Glyceryl Linolenate, Glyceryl Arachidonate) | 0.50% |
| I | Mono-and Distearate Esters of Polyoxyethylene and Free Polyethylene Oxide | 1.25% |
| I | Partial Esters of Lauric, Palmitic, Stearic and Oleic Acids and Hexitol Anhydrides | 0.13% |
| I | 120-Mole Ethoxylated Jojoba Oil | 1.0% |
| I | Polyoxyethylene Fatty Acid Esters | 2.5% |
| I | Cetyl Alcohol | 4.0% |
| I | White Petrolatum | 3.0% |
| I | Tricaprylin | 5.5% |
| I | Mineral Oil | 6.0% |
| I | Complex of Propylene Glycol, Propyl Gallate, and Citric Acid | 0.011% |
| II | Demineralized Water | 55.5471% |
| II | Imidazolyl Urea | 0.0011% |
| II | Complex of Propylene Glycol, Phenoxyethanol, Chlorphenesin, and Methylparaben | 2.5% |
| III | 1,3-Butylene Glycol | 4.0% |
| III | Alginate Derivatives | 0.2% |
| IV | Tricaprylin | 2.0% |
| IV | Preneutralized Carbomer 430 | 0.5% |
| V | First Complex of Water, Propylene Glycol, Lecithin, Caffeine Benzoate, and Palmitoyl Carnitine | 3.0% |
| V | Second Complex of Water, Caffeine, Carnitine, and Hydrolyzed Glycosaminoglycans | 2.0% |
| VI | Third Complex of Glycerol, Butcher Broom Extract, Passion Flower Extract, Glycogen, Hydrolyzed Collagen, and PEG 6-32 | 0.0011% |
| VI | Calendula Extract | 0.2% |
| VI | Aloe Vera Gel | 0.2% |
| VI | Water-Glycol Extract of Chamomile | 0.2% |
| VI | Polar Complex | 1.0% |
| VI | Glycosaminoglycans | 1.0% |
| VII | Hydrophilic Microcapsules | |
| VII | Lipophilic Microcapsules | |
| VII | Microcapsules Comprising Methylsilanol Elastinate | |
| VIII | Nylon-12 | 1.2% |
| IX | Fragrance | 0.45% |

I claim:

1. A skin cream composition comprising: water and emulsified and dispersed in the water:
   (a) a long-chain fatty acid ester of ascorbic acid;
   (b) a short-chain carboxylic acid ester of tocopherol;
   (c) a glyceryl ester complex comprising at least one glyceryl ester selected from the group consisting of glyceryl linoleate, glyceryl linolenate, and glyceryl arachidonate;
   (d) a first complex consisting essentially of water, propylene glycol, lecithin, caffeine benzoate, and palmitoyl carnitine;
   (e) a second complex consisting essentially of water, caffeine, carnitine, and hydrolyzed glycosaminoglycans;
   (f) a third complex consisting essentially of glycerol, butcher broom extract, passion flower extract, glycogen, hydrolyzed collagen, and PEG 6-32;
   (g) calendula extract;
   (h) a water-glycol extract of chamomile;
   (i) hydrophilic microcapsules;
   (j) lipophilic microcapsules; and
   (k) microcapsules comprising methylsilanol elastinate; wherein each of the long-chain fatty acid ester of ascorbic acid, the short-chain carboxylic acid ester of tocopherol, the glyceryl ester complex, the first complex, the second complex, the third complex, the calendula extract, the water-glycol extract of chamomile, the hydrophilic microcapsules, the lipophilic microcapsules, and the microcapsules comprising methylsilanol elastinate are present in a quantity sufficient to increase the smoothness, decrease the lumpiness, or decrease the edema of skin to which the composition is applied.

2. The skin cream composition of claim 1 further comprising aloe vera gel.

3. The skin cream composition of claim 1 further comprising glycosaminoglycans.

4. The skin cream composition of claim 1 further comprising nylon-12.

5. The skin cream composition of claim 1 further comprising aloe vera gel, glycosaminoglycans, and nylon-12.

6. The skin cream composition of claim 1 wherein the long-chain fatty acid ester of ascorbic acid is selected from the group consisting of ascorbyl palmitate, ascorbyl myristate, and ascorbyl stearate.

7. The skin cream composition of claim 1 wherein the long-chain fatty acid ester of ascorbic acid is ascorbyl palmitate.

8. The skin cream composition of claim 1 wherein the short-chain carboxylic acid ester of tocopherol is selected from the group consisting of tocopheryl acetate, tocopheryl propionate, and tocopheryl butyrate.

9. The skin cream composition of claim 1 wherein the short-chain carboxylic acid ester of tocopherol is tocopheryl acetate.

10. The skin cream composition of claim 1 wherein the glyceryl ester complex comprises glyceryl linoleate, glyceryl linolenate, and glyceryl arachidonate.

11. The cosmetic composition of claim 1 wherein the hydrophilic microcapsules comprise in water:
   (a) glycerol;
   (b) chitin;
   (c) sodium lactate;
   (d) sodium pyrrolidone carboxylate;
   (e) glycogen;
   (f) urea;
   (g) propylene glycol;
   (h) sodium chloride;
   (i) at least one amino acid selected from the group consisting of glycine, arginine, lysine, histidine, and ornithine; and
   (j) hydrolyzed collagen.

12. The skin cream composition of claim 11 wherein the hydrophilic microcapsules comprise glycine, arginine, lysine, histidine, and ornithine.

13. The skin cream composition of claim 1 wherein the lipophilic microcapsules comprise:
    (a) glycosphingolipids;
    (b) phospholipids;
    (c) cholesterol;
    (d) at least one long-chain saturated fatty acid selected from the group consisting of myristic acid, palmitic acid, stearic acid, and arachidic acid;
    (e) squalane;
    (f) a $C_{10}$–$C_{30}$ carboxylic acid ester of a sterol selected from the group consisting of cholesterol, lanosterol, and mixtures thereof; and
    (g) octyldodecanol.

14. The skin cream composition of claim 13 wherein the lipophilic microcapsules comprise stearic acid and palmitic acid.

15. The skin cream composition of claim 14 wherein the lipophilic microcapsules further comprise a diglyceryl succinate of a medium-chain carboxylic acid selected from the group consisting of caprylic acid, capric acid, and mixtures thereof.

16. The skin cream composition of claim 5 wherein the hydrophilic microcapsules comprise, in water: glycerol, chitin, sodium lactate, sodium pyrrolidone carboxylate, glycogen, urea, propylene glycol, glycine, arginine, lysine, histidine, and ornithine, the lipophilic microcapsules comprise glycosphingolipids, phospholipids, cholesterol, stearic acid, palmitic acid, squalane, a $C_{10}$–$C_{30}$ carboxylic acid ester of a sterol selected from the group consisting of cholesterol, lanosterol, and mixtures thereof, octyldodecanol, and a diglyceryl succinate of a medium-chain fatty acid selected from the group consisting of caprylic acid, capric acid, and mixtures thereof, the long-chain fatty acid ester of ascorbic acid is ascorbyl palmitate, and the short-chain carboxylic acid ester of tocopherol is tocopheryl acetate.

17. The skin cream composition of claim 16 wherein the ascorbyl palmitate comprises about 0.02% of the composition, the tocopheryl acetate comprises about 0.5% of the composition, the glyceryl ester complex comprises about 0.5% of the composition, the first complex comprises about 3.0% of the composition, the second complex comprises about 2.0% of the composition, the third complex comprises about 0.0011% of the composition, the calendula extract comprises about 0.2% of the composition, the aloe vera gel comprises about 0.2% of the composition, the water-glycol extract of chamomile comprises about 0.2% of the composition, the glycosaminoglycans comprise about 1.0% of the composition, the hydrophilic microcapsules comprise about 0.25% of the composition, the lipophilic microcapsules comprise about 0.25% of the composition, the microcapsules comprising methylsilanol elastinate comprise about 0.25% of the composition, and the nylon-12 comprises about 1.2% of the composition.

18. The cosmetic composition of claim 1 further comprising a lipid-soluble component.

19. The skin cream composition of claim 18 wherein the lipid-soluble component comprises at least one of dimethicone, bisabolol, polyoxyethylene fatty acid esters, cetyl alcohol, a glyceryl triester of a medium-chain carboxylic acid selected from the group consisting of tricaproin, tricaprylin, and tricaprin, and mixtures thereof, white petrolatum, and mineral oil.

20. The skin cream composition of claim 19 wherein the lipid-soluble component comprises dimethicone, bisabolol, polyoxyethylene fatty acid esters, cetyl alcohol, tricaprylin, white petrolatum, and mineral oil, and wherein the dimethicone comprises about 0.75% of the composition, the bisabolol comprises about 0.10% of the composition, the polyoxyethylene fatty acid esters comprise about 2.5% of the composition, the cetyl alcohol comprises about 4% of the composition, the tricaprylin comprises about 7.5% of the composition, the white petrolatum comprises about 3% of the composition, and the mineral oil comprises about 6.0% of the composition.

21. The skin cream composition of claim 1 further comprising an emulsifier component.

22. The skin cream composition of claim 21 wherein the emulsifier component comprises at least one of a mixture of mono- and distearate esters of polyoxyethylene and free polyethylene oxide, partial esters of lauric, palmitic, stearic, and oleic acids and hexitol anhydrides, and 120-mole ethoxylated jojoba oil.

23. The skin cream composition of claim 22 wherein the emulsifier component comprises a mixture of mono- and distearate esters of polyoxyethylene and free polyethylene oxide, partial esters of lauric, palmitic, stearic, and oleic acids and hexitol anhydrides, and 120-mole ethoxylated jojoba oil, and the mixture of mono- and distearate esters of polyoxyethylene and free polyethylene oxide comprises about 1.25% of the composition, the partial esters of lauric, palmitic, stearic, and oleic acids and hexitol anhydrides comprise about 0.13% of the composition, and the 120-mole ethoxylated jojoba oil comprises about 1.0% of the composition.

24. The skin cream composition of claim 1 further comprises an antioxidant component.

25. The skin cream composition of claim 23 wherein the antioxidant component comprises a mixture of about 70% propylene glycol, about 20% propyl gallate, and about 10% citric acid, and the antioxidant component comprises about 0.0011% of the composition.

26. The skin cream composition of claim 1 further comprising a preservative component.

27. The skin cream composition of claim 26 wherein the preservative component comprises at least one of imidazolyl urea and a complex of propylene glycol, phenoxyethanol, chlorphenesin, and methylparaben.

28. The skin cream composition of claim 27 wherein the preservative component comprises imidazolyl urea and a complex of propylene glycol, phenoxyethanol, chlorphenesin, and methylparaben, the imidazolyl urea comprises about 0.0011% of the composition, and the complex of propylene glycol, phenoxyethanol, chlorphenesin, and methylparaben comprises about 2.5% of the composition.

29. The skin cream composition of claim 1 further comprising a solvent component.

30. The skin cream composition of claim 29 wherein the solvent component includes at least one ingredient selected from the group consisting of ethylene glycol, propylene glycol and 1,3-butylene glycol.

31. The skin cream composition of claim 30 wherein the solvent component comprises 1,3-butylene glycol and the 1,3-butylene glycol comprises about 4.0% of the composition.

32. The skin cream composition of claim 1 further comprising a thickener component.

33. The skin cream composition of claim 32 wherein the thickener component comprises at least one ingredient selected from the group consisting of alginate derivatives and preneutralized carbomer 430.

34. The skin cream composition of claim 33 wherein the thickener component comprises both alginate derivatives and preneutralized carbomer 430, and wherein the alginate derivatives comprise about 0.2% of the composition and the preneutralized carbomer 430 comprises about 0.5% of the composition.

35. The skin cream composition of claim 1 further comprising a hydrophilic component.

36. The skin cream composition of claim 35 wherein the hydrophilic component is a polar complex consisting essentially of mannitol, arginine, serine, pyrrolidone carboxylate, sucrose, citrulline, glycogen, histidine, alanine, threonine, glutamic acid, and lysine, wherein the mannitol, the arginine, the serine, the pyrrolidone carboxylate, the sucrose, the citrulline, the glycogen, the histidine, the alanine, and the threonine each comprise from about 2% to about 20% of the polar complex, and the glutamic acid and lysine each comprise from about 0.1% to about 2.0% of the polar complex, and the polar complex comprises about 1.0% of the composition.

37. The skin cream composition of claim 1 further comprising fragrance.

38. The skin cream composition of claim 37 wherein the fragrance comprises about 0.45% of the composition.

39. A skin cream composition comprising water, and emulsified and dispersed in the water:
  (a) ascorbyl palmitate;
  (b) tocopheryl acetate;
  (c) a glyceryl ester complex comprising glyceryl linoleate, glyceryl linolenate, and glyceryl arachidonate;
  (d) a complex consisting essentially of water, propylene glycol, lecithin, caffeine benzoate, and palmitoyl carnitine;
  (e) a complex consisting essentially of caffeine, carnitine, and hydrolyzed glycosaminoglycans;
  (f) a complex consisting essentially of glycerol, butcher broom extract, passion flower extract, glycogen, hydrolyzed collagen, and PEG 6-32;
  (g) calendula extract;
  (h) a water-glycol extract of chamomile;
  (i) hydrophilic microcapsules comprising in water:
    (1) glycerol;
    (2) chitin;
    (3) sodium lactate;
    (4) sodium pyrrolidone carboxylate;
    (5) glycogen;
    (6) urea;
    (7) propylene glycol;
    (8) sodium chloride;
    (9) glycine;
    (10) arginine;
    (11) lysine;
    (12) histidine;
    (13) ornithine; and
    (14) hydrolyzed collagen;
  (j) lipophilic microcapsules comprising:
    (1) glycosphingolipids;
    (2) phospholipids;
    (3) cholesterol;
    (4) stearic acid;
    (5) palmitic acid;
    (6) squalane;
    (7) a $C_{10}$–$C_{30}$ carboxylic acid ester of a sterol selected from the group consisting of cholesterol, lanosterol, and mixtures thereof;
    (8) a diglyceryl succinate of a medium-chain carboxylic acid selected from the group consisting of caprylic acid, capric acid, and mixtures thereof; and
    (9) octyldodecanol;
  (k) microcapsules comprising methylsilanol elastinate;
  (l) glycosaminoglycans;
  (m) aloe vera gel;
  (n) nylon-12;
  (o) a lipid-soluble component comprising:
    (1) dimethicone;
    (2) bisabolol;
    (3) polyoxyethylene fatty acid esters;
    (4) cetyl alcohol;
    (5) white petrolatum;
    (6) tricaprylin; and
    (7) mineral oil;
  (p) an emulsifier component comprising:
    (1) a mixture of mono- and distearate esters of polyoxyethylene and free polyethylene oxide;
    (2) partial esters of lauric, palmitic, stearic, and oleic acids and hexitol anhydrides; and
    (3) 120-mole ethoxylated jojoba oil;
  (q) an antioxidant component comprising a mixture of 70% propylene glycol, 20% propyl gallate, and 10% citric acid;
  (r) a preservative component comprising:
    (1) imidazolyl urea; and
    (2) a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11 to about 22% of the complex;
  (s) a solvent component comprising 1,3-butylene glycol;
  (t) a thickener component comprising:
    (1) alginate derivatives; and
    (2) preneutralized carbomer 430; and
  (u) a hydrophilic component comprising a polar complex consisting essentially of mannitol, arginine, serine, pyrrolidone carboxylate, sucrose, citrulline, glycogen, histidine, alanine, threonine, glutamic acid, and lysine, wherein the mannitol, the arginine, the serine, the pyrrolidone carboxylate, the sucrose, the citrulline, the glycogen, the histidine, the alanine, and the threonine each comprise from about 2% to about 20% of the polar complex, and the glutamic acid and the lysine each comprises from about 0.1% to about 2% of the polar complex; wherein each of the long-chain fatty acid ester of ascorbic acid, the short-chain carboxylic acid ester of tocopherol, the glyceryl ester complex, the first complex, the second complex, the third complex, the calendula extract, the water-glycol extract of chamomile, the hydrophilic microcapsules, the lipophilic microcapsules, the microcapsules comprising methylsilanol elastinate, the glycosaminoglycans, the aloe vera gel, and the nylon-12 are present in a quantity sufficient to increase the smoothness, decrease the lumpiness, or decrease the edema of skin to which the composition is applied.

40. The skin cream composition of claim 39 wherein the ascorbyl palmitate comprises about 0.02% of the composition, the tocopheryl acetate comprises about 0.5% of the composition, the glyceryl ester complex comprises about 0.5% of the composition, the first complex comprises about 3.0% of the composition, the second complex comprises about 2.0% of the composition, the third complex comprises about 0.0011% of the composition, the calendula extract comprises about 0.2% of the composition, the aloe vera gel comprises about 0.2% of the composition, the water-glycol extract of chamomile comprises about 0.2% of the composition, the glycosaminoglycans comprise about 1.0% of the composition, the hydrophilic microcapsules comprise about 2.5% of the composition, the lipophilic microcapsules comprise about 0.25% of the composition, the microcapsules comprising methylsilanol elastinate comprise about 0.25% of the composition, and the nylon-12 comprises about 1.2% of the composition.

41. A skin cream composition comprising: water, and emulsified and dispersed in the water;
    (a) about 0.75% of dimethicone;
    (b) about 0.1% of bisabolol;
    (c) about 0.02% of ascorbyl palmitate;
    (d) about 0.5% of tocopheryl acetate;
    (e) about 0.5% of a glyceryl ester complex comprising glyceryl linoleate, glyceryl linolenate, and glyceryl arachidonate, wherein the glyceryl linoleate comprises from about 65% to about 85% of the complex, the glyceryl linolenate comprises from about 5% to about 15% of the complex, and the glyceryl arachidonate comprises from about 1% to about 5% of the complex;
    (f) about 1.25% of a mixture of mono- and distearate esters of polyoxyethylene and free polyethylene oxides;
    (g) about 0.13% of partial esters of lauric, palmitic, stearic, and oleic acids and hexitol anhydrides;
    (h) about 1.0% of 120-mole ethoxylated jojoba oil;
    (i) about 2.5% of polyoxyethylene fatty acid esters;
    (j) about 4.0% of cetyl alcohol;
    (k) about 3.0% of white petrolatum;
    (l) about 7.50% of tricaprylin;
    (m) about 6.0% of mineral oil;
    (n) about 0.0011% of a mixture of 70% propylene glycol, 20% propyl gallate, and 10% citric acid;
    (o) about 0.0011% of imidazolyl urea;
    (p) about 2.5% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
    (q) about 4.0% of 1,3-butylene glycol;
    (r) about 0.2% of alginate derivatives;
    (s) about 0.5% of preneutralized carbomer 430;
    (t) about 3.0% of a first complex consisting essentially of water, propylene glycol, lecithin, caffeine benzoate and palmitoyl carnitine;
    (u) about 2.0% of a second complex consisting essentially of water, caffeine, carnitine, and hydrolyzed glycosaminoglycans;
    (v) about 0.0011% of a complex consisting essentially of glycerol, butcher broom extract, passion flower extract, glycogen, hydrolyzed collagen, and PEG 6-32;
    (w) about 0.2% of calendula extract;
    (x) about 0.2% of aloe vera gel;
    (y) about 0.2% of a water-glycol extract of chamomile;
    (z) about 1.0% of a polar complex consisting essentially of mannitol, arginine, serine, pyrrolidone carboxylate, sucrose, citrulline, glycogen, histidine, alanine, threonine, glutamic acid, and lysine, wherein the mannitol, the arginine, the serine, the pyrrolidone carboxylate, the sucrose, the citrulline, the glycogen, the histidine, the alanine, and the threonine each comprise from about 2% to about 20% of the complex, and the glutamic acid and the lysine each comprise from about 0.1% to about 2% of the complex;
    (aa) about 1.0% of glycosaminoglycans;
    (ab) about 0.25% of hydrophilic microcapsules, the hydrophilic microcapsules comprising in water:
        (1) from about 20% to about 40% glycerol;
        (2) from about 10% to about 20% chitin;
        (3) from about 5% to about 15% each of sodium lactate and sodium pyrrolidone carboxylate;
        (4) from about 1% to about 5% each of glycogen, urea, propylene glycol, and sodium chloride;
        (5) up to about 1% each of glycine, arginine, lysine, histidine, and ornithine; and
        (6) up to about 1% of hydrolyzed collagen;
    (ac) about 0.25% of lipophilic microcapsules, the lipophilic microcapsules comprising:
        (1) from about 5% to about 15% each of glycosphingolipids, phospholipids, and cholesterol;
        (2) from about 1% to about 5% each of stearic acid, palmitic acid, squalane, and a $C_{10}$–$C_{30}$ carboxylic acid ester of a sterol selected from the group consisting of cholesterol, lanosterol, and mixtures thereof;
        (3) up to about 1% of a diglyceryl succinate of a medium-chain carboxylic acid selected from the group consisting of caprylic acid, capric acid, and mixtures thereof; and
        (4) from about 60% to about 80% of octyldodecanol;
    (ad) about 0.25% of microcapsules comprising methylsilanol elastinate;
    (ae) about 1.2% of nylon-12; and
    (af) about 0.45% of fragrance.

42. A skin cream composition comprising water, and emulsified and dispersed in the water:
    (a) ascorbyl palmitate;
    (b) tocopheryl acetate;
    (c) a glyceryl ester complex comprising glyceryl linoleate, glyceryl linoleate, and glyceryl arachidonate;
    (d) a complex consisting essentially of water, propylene glycol, lecithin, caffeine benzoate, and palmitoyl carnitine;
    (e) a complex consisting essentially of caffeine, carnitine, and hydrolyzed glycosaminoglycans;
    (f) a complex consisting essentially of glycerol, butcher broom extract, passion flower extract, glycogen, hydrolyzed collagen, and PEG 6-32;
    (g) calendula extract;
    (h) a water-glycol extract of chamomile;
    (i) hydrophilic microcapsules comprising in water:
        (1) glycerol;
        (2) chitin;
        (3) sodium lactate;
        (4) sodium pyrrolidone carboxylate;
        (5) glycogen;

(6) urea;
(7) propylene glycol;
(8) sodium chloride;
(9) glycine;
(10) arginine;
(11) lysine;
(12) histidine;
(13) ornithine; and
(14) hydrolyzed collagen;
(j) lipophilic microcapsules comprising:
  (1) glycosphingolipids;
  (2) phospholipids;
  (3) cholesterol;
  (4) stearic acid;
  (5) palmitic acid;
  (6) squalane;
  (7) a $C_{10}$–$C_{30}$ carboxylic acid ester of a sterol selected from the group consisting of cholesterol, lanosterol, and mixtures thereof;
  (8) a diglyceryl succinate of a medium-chain carboxylic acid selected from the group consisting of caprylic acid, capric acid, and mixtures thereof; and
  (9) octyldodecanol;
(k) microcapsules comprising methylsilanol elastinate;
(l) glycosaminoglycans;
(m) aloe vera gel;
(n) nylon-12;
(o) a lipid-soluble component comprising:
  (1) dimethicone;
  (2) bisabolol;
  (3) polyoxyethylene fatty acid esters;
  (4) cetyl alcohol;
  (5) white petrolatum;
  (6) tricaprylin; and
  (7) mineral oil;
(p) an emulsifier component comprising:
  (1) a mixture of mono- and distearate esters of polyoxyethylene and free polyethylene oxide;
  (2) partial esters of lauric, palmitic, stearic, and oleic acids and hexitol anhydrides; and
  (3) 120-mole ethoxylated jojoba oil;
(q) an antioxidant component comprising a mixture of 70% propylene glycol, 20% propyl gallate, and 10% citric acid;
(r) a preservative component comprising:
  (1) imidazolyl urea; and
  (2) a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(s) a solvent component comprising 1,3-butylene glycol; and
(t) a hydrophilic component comprising a polar complex consisting essentially of mannitol, arginine, serine, pyrrolidone carboxylate, sucrose, citrulline, glycogen, histidine, alanine, threonine, glutamic acid, and lysine, wherein the mannitol, the arginine, the serine, the pyrrolidone carboxylate, the sucrose, the citrulline, the glycogen, the histidine, the alanine, and the threonine each comprise from about 2% to about 20% of the polar complex, and the glutamic acid and the lysine each comprise from about 0.1% to about 2% of the polar complex;

wherein each of the long-chain fatty acid ester of ascorbic acid, the short-chain carboxylic acid ester of tocopherol, the glycerol ester complex, the first complex, the second complex, the third complex, the calendula extract, the water-glycol extract of chamomile, the hydrophilic microcapsules, the lipophilic microcapsules, the microcapsules comprising methylsilanol elastinate, the glycosaminoglycans, the aloe vera gel, and the nylon-12 are present in a quantity sufficient to increase the smoothness, decrease the lumpiness, or decrease the edema of skin to which the composition is applied.

43. The skin cream composition of claim 42 wherein the ascorbyl palmitate comprises about 0.02% of the composition, the tocopheryl acetate comprises about 0.5% of the composition, the glyceryl ester complex comprises about 0.5% of the composition, the first complex comprises about 3.0% of the composition, the second complex comprises about 2.0% of the composition, the third complex comprises about 0.0011% of the composition, the calendula extract comprises about 0.2% of the composition, the aloe vera gel comprises about 0.2% of the composition, the water-glycol extract of chamomile comprises about 0.2% of the composition, the glycosaminoglycans comprise about 1.0% of the composition, the lipophilic microcapsules comprise about 0.25% of the composition, the microcapsules comprising methylsilanol elastinate comprise about 0.25% of the composition, and the nylon-12 comprises about 1.2% of the composition.

44. A skin cream composition comprising: water and emulsified and dispersed in the water:
(a) about 0.75% of dimethicone;
(b) about 0.1% of bisabolol;
(c) about 0.02% of ascorbyl palmitate;
(d) about 0.5% of tocopheryl acetate;
(e) about 0.05% of a glyceryl ester complex comprising glyceryl linoleate, glyceryl linolenate, and glyceryl arachidonate, wherein the glyceryl linoleate comprises from about 65% to about 85% of the complex, the glyceryl linolenate comprises from about 5% to about 15% of the complex, and the glyceryl arachidonate comprises from about 1% to about 5% of the complex;
(f) about 1.25% of a mixture of mono-and distearate esters of polyoxyethylene and free polyethylene oxides;
(g) about 0.13% of partial esters of lauric, palmitic, stearic, and oleic acids and hexitol anhydrides;
(h) about 1.0% of 120-mole ethoxylated jojoba oil;
(i) about 2.5% of polyoxyethylene fatty acid esters;
(j) about 4.0% of cetyl alcohol;
(k) about 3.0% of white petrolatum;
(l) about 7.5% of tricaprylin;
(m) about 6.0% of mineral oil;
(n) about 0.0011% of a mixture of 70% propylene glycol, 20% propyl gallate, and 10% citric acid;
(o) about 0.0011% of imidazolyl urea;
(p) about 2.5% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(q) about 4.0% of 1,3-butylene glycol;

(r) about 3.0% of a first complex consisting essentially of water, propylene glycol, lecithin, caffeine benzoate, and palmitoyl carnitine;

(s) about 2.0% of a second complex consisting essentially of water, caffeine, carnitine, and hydrolyzed glycosaminoglycans;

(t) about 0.0011% of a complex consisting essentially of glycerol, butcher broom extract, passion flower extract, glycogen, hydrolyzed collagen, and PEG 6-32;

(u) about 0.2% of calendula extract;

(v) about 0.2% of aloe vera gel;

(w) about 0.2% of a water-glycol extract of chamomile;

(x) about 1.0% of a polar complex consisting essentially of mannitol, arginine, serine, pyrrolidone carboxylate, sucrose, citrulline, glycogen, histidine, alanine, threonine, glutamic acid, and lysine, wherein the mannitol, the arginine, the serine, the pyrrolidone carboxylate, the sucrose, the citrulline, the glycogen, the histidine, the alanine, and the threonine each comprise from about 2% to about 20% of the complex, and the glutamic acid and the lysine each comprise from about 0.1% to about 2% of the complex;

(y) about 1.0% of glycosaminoglycans;

(z) about 0.25% of hydrophilic microcapsules, the hydrophilic microcapsules comprising in water:
  (1) from about 20% to about 40% glycerol;
  (2) from about 10% to about 20% chitin;
  (3) from about 5% to about 15% each of sodium lactate and sodium pyrrolidone carboxylate;
  (4) from about 1% to about 5% each of glycogen, urea, propylene glycol, and sodium chloride;
  (5) up to about 1% each of glycine, arginine, lysine, histidine, and ornithine; and
  (6) up to about 1% of hydrolyzed collagen;

(aa) up to about 0.25% of lipophilic microcapsules, the lipophilic microcapsules comprising:
  (1) from about 5% to about 15% each of glycosphingolipids, phospholipids, and cholesterol;
  (2) from about 1% to about 5% each of stearic acid, palmitic acid, squalane, and a $C_{10}$–$C_{30}$ carboxylic acid ester of a sterol selected from the group consisting of cholesterol, lanosterol and mixtures thereof;
  (3) up to about 1% of a diglyceryl succinate of a medium-chain carboxylic acid selected from the group consisting of caprylic acid, capric acid, and mixtures thereof; and
  (4) from about 60% to about 80% of octyldodecanol;

(ab) about 0.25% of microcapsules comprising methylsilanol elastinate;

(ac) about 1.2% of nylon-12; and (ad) about 0.45% of fragrance.

* * * * *